(12) United States Patent
Tiwari et al.

(10) Patent No.: US 7,951,754 B2
(45) Date of Patent: May 31, 2011

(54) ENVIRONMENTALLY FRIENDLY BIS-QUATERNARY COMPOUNDS FOR INHIBITING CORROSION AND REMOVING HYDROCARBONACEOUS DEPOSITS IN OIL AND GAS APPLICATIONS

(75) Inventors: Laxmikant Tiwari, Southampton (GB); G. Richard Meyer, Missouri City, TX (US); David Horsup, Bellaire, TX (US)

(73) Assignee: Nalco Company, Naperville, IL (US)

( * ) Notice: Subject to any disclaimer, the term of this patent is extended or adjusted under 35 U.S.C. 154(b) by 238 days.

(21) Appl. No.: 11/952,211

(22) Filed: Dec. 7, 2007

(65) Prior Publication Data

US 2009/0149356 A1    Jun. 11, 2009

(51) Int. Cl.
*C09K 8/52* (2006.01)
*C09K 8/524* (2006.01)
*E21B 43/28* (2006.01)
(52) U.S. Cl. .......................... 507/90; 507/939; 166/275
(58) Field of Classification Search .................. 507/939, 507/90; 166/275
See application file for complete search history.

(56) References Cited

U.S. PATENT DOCUMENTS

| 3,578,592 | A | | 5/1971 | Pontelandolfo | |
| 5,611,992 | A | * | 3/1997 | Naraghi et al. | 422/15 |
| 6,234,183 | B1 | | 5/2001 | Chan et al. | |
| 6,303,079 | B1 | * | 10/2001 | Meyer | 422/12 |
| 2006/0013798 | A1 | * | 1/2006 | Henry et al. | 424/78.09 |

OTHER PUBLICATIONS

Written Opinion of the International Searching Authority for PCT/US2008/085789.
International Search Report and Written Opinion of the International Searching Authority PCT/US2008/085789.

* cited by examiner

*Primary Examiner* — Timothy J. Kugel
*Assistant Examiner* — Aiqun Li
(74) *Attorney, Agent, or Firm* — Edward O. Yonter; Michael B. Martin

(57) ABSTRACT

Environmentally friendly compounds for corrosion inhibition and hydrocarbonaceous deposit removal and methods using such compounds are disclosed and claimed. The compounds are derivatives of heterocyclic bis-quaternary molecules having an amido moiety and are applicable to a variety of oil and gas operations.

20 Claims, No Drawings

ENVIRONMENTALLY FRIENDLY BIS-QUATERNARY COMPOUNDS FOR INHIBITING CORROSION AND REMOVING HYDROCARBONACEOUS DEPOSITS IN OIL AND GAS APPLICATIONS

TECHNICAL FIELD

This invention relates generally to compositions and methods for environmentally friendly oil and gas industry corrosion inhibitors and schmoo removers. More specifically, the invention relates to compositions including bis-quaternary compounds and methods useful for removing schmoo from and preventing corrosion in oilfield and refinery equipment. The invention has particular relevance to environmentally friendly bis-quaternary compounds having an amido moiety.

BACKGROUND

To meet the significant growth in oil and gas demand today, exploration is moving to uncharted, ultra-deep water locations and production is being considered in locations previously considered to be off-limits. Further, much of the existing infrastructure typically operates well beyond its designed capabilities. This overreach creates significant technical challenges in all areas of production; however, no challenge is more difficult than preserving infrastructure integrity.

Corrosion inhibitors are frequently introduced into oil and gas fluids to aid in maintaining infrastructure integrity. Corrosion inhibitors are added to a wide array of systems and system components, such as cooling systems, refinery units, pipelines, steam generators, and oil or gas producing and production water handling equipment. These corrosion inhibitors are geared towards combating a large variety of corrosion types. For example, a common type of corrosion encountered in the transport of fluid having one or more corrosive agents is flow-induced corrosion, where the degree of corrosion depends on a multitude of factors. These factors include the corrosiveness of the fluid, pipeline metallurgy, shear rate, temperature, and pressure.

Injection of a high performance inhibitor at the appropriate location and optimum dosage can be extremely effective at reducing corrosion rates, such as on pipe walls. Observing a greater than 95% decrease in corrosion is not uncommon. Performance is typically determined through several techniques, such as electrical resistance probes, coupon measurements, and inspection readings. In some cases, however, corrosion inhibitor performance may deteriorate over time, particularly in systems that have a tendency to accumulate significant quantities of solids.

Depending on the particular system, these solids can build up to form a layer up to several centimeters thick. Deposits of such hydrocarbonaceous materials and finely divided inorganic solids form on the inner surfaces of the lines. These deposits may include, for example, sand, clays, sulfur, napthenic acid salts, corrosion byproducts, and biomass bound together with oil. The particles become coated with corrosion inhibitor or other hydrocarbonaceous materials and subsequently become coated with additional quantities of heavy hydrocarbonaceous material in the flowlines, settling tank, and the like. Collectively, this layer is often referred to as "schmoo" in the petroleum industry.

Schmoo is a solid or paste-like substance that adheres to almost any surface with which it comes in contact and is particularly difficult to remove. Whenever possible, pipelines known to have such deposited materials or that form pools of water at low spots are routinely pigged to remove the material. In many cases, however, it may not be feasible to pig lines due to the construction configuration, variable pipeline diameter, or the lack of pig launchers and receivers. The material often accumulates on, for example, the bottom or around the circumference of the pipe. Additionally, even after maintenance pigging, schmoo still often resides inside pits in metal surfaces. As discussed above, these situations create a significant risk for increased corrosion. Schmoo can also accumulate to a thickness such that it flakes off the inner surfaces of the pipe and deposits in the lower portion of a well, the lower portion of a line or the like, and plugs the line or the formation in fluid communication with the pipe.

The physical barrier formed by such a layer also retards the diffusion of corrosion inhibitors to the pipe wall. These solids also often have a strong affinity for corrosion inhibitors and may significantly reduce inhibitor availability in situ. Furthermore, the composition of matter within the solids forms an ideal environment to foster bacterial growth, the metabolic byproducts of which are frequently highly corrosive. This microbiologically influenced corrosion process has been recognized as a significant problem in the industry for many years. Additional challenges are encountered in water injection systems when material carried in the water causes plugging of the sand-face downhole. Such plugging often leads to reduction in water injection efficiency and a consequent reduction of the oil produced.

Moreover, stringent governmental regulations have imposed environmental constraints on the oil and gas producing industry. These regulations have led to the need for new "greener" chemistries, which have reduced environmental impact. The environmental impact of any chemical is typically defined by three criteria: biodegradation, bioaccumulation, and toxicity. All three criteria have benchmarks that must be met for a chemical to be permitted for use, with different emphasis on each depending on which regulatory body controls the waters. This environmental drive has been spearheaded by North Sea Regulators (e.g., CEFAS) and their success has sparked similar programs, currently being implemented in other oil producing regions. Operators now demand identical levels of performance with existing treatments along with the fulfillment of the new environmental criteria for any chemicals that may be contained, for example, in rig overboard discharge.

In view of these difficulties there exists an ongoing need for improved and environmentally friendly methods of removing deposits from pipelines to optimize oil production, particularly where water injection systems are used. An ideal solution would include a chemical-based process to remove the deposits, prevent further deposits from forming in the system, and optimize water volume (in many cases including maximizing water injectivity). Simultaneously protecting the system from corrosion caused by the presence of naturally occurring acidic species and bacterial byproducts would also be highly desirable.

SUMMARY

This invention accordingly provides novel compositions and methods for inhibiting corrosion and removing hydrocarbonaceous deposits in oil and gas applications. The disclosed bis-quaternary corrosion inhibitors and schmoo removers have low environmental impact and exhibit superior performance. The compounds and compositions of the invention can be used in any system exposed to fluids (i.e., liquid, gas, slurry, or mixture thereof) containing a metal corrosion agent where improved corrosion inhibition is desired. Moreover, the compositions of the invention may be used in any component or any part of the oil and gas system where hydrocarbonaceous deposits are a concern, including, for example, flowlines, pipelines, injection lines, wellbore surfaces, and the like.

In an aspect, the invention provides a bis-quaternized compound for inhibiting corrosion and/or removing hydrocarbonaceous deposits in oil and gas applications. In a preferred embodiment the compound (referred to as Structure I) has the following general formula:

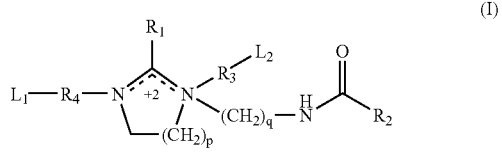

(I)

$R_1$, $R_2$, $R_3$, and $R_4$ are independently selected from the group consisting of unsubstituted branched, chain, or ring alkyls or alkenyls that have from 1 to about 29 carbon atoms; partially or fully oxygenized, sulfurized, and/or phosphorylized branched, chain, or ring alkyls or alkenyls having from 1 to about 29 carbon atoms; and their combinations.

$L_1$ and $L_2$ are each a moiety independently selected from the group consisting of —H, —$CO_2H$, —$SO_3H$, —$PO_3H_2$, —$CO_2R_5$, —$CONH_2$, —$CONHR_5$, —$CON(R_5)_2$, and combinations thereof. In an embodiment, each $R_5$ is independently selected from branched or unbranched alkyl, aryl, alkylaryl, cycloalkyl, and heteroaromatic groups having from 1 to about 10 carbon atoms, and their combinations.

In an embodiment, p is from 1 to about 5. In an embodiment, q is from 1 to about 10.

It should be appreciated that the number of carbon atoms specified for each group described herein refers to the main chain of carbon atoms and does not include carbon atoms that may be contributed by substituents.

According to another aspect, the invention is a method of using the compound depicted as Structure I for improving production in an oil and/or gas application, such as by reducing a corrosion rate of and/or removing hydrocarbonaceous deposits from metallic or mineral surfaces in contact with a fluid in oil and gas applications. The method includes adding to the fluid. (i) a compound of Structure I in either pure or mixed solid form to the fluid or (ii) a composition having from about 5 to about 50 weight percent of the compound of Structure I dispersed or dissolved in one or more solvents.

In a further aspect of the invention, a method of producing a composition including at least one bis-quaternized compound having the general formula of Structure I is provided. The method includes selecting a first organic acid from unsubstituted saturated or mono- or poly unsaturated fatty acids having from 1 to about 30 carbon atoms; partially or fully substituted saturated or mono- or poly unsaturated fatty acids having from about 1 to about 30 carbon atoms, wherein said substitution includes being oxygenized, sulfurized, and/or phosphorylized; and combinations thereof. In an embodiment, the first organic acid has from about 6 to about 30 carbon atoms.

The method further includes selecting an alkyl polyamine from the group having a general formula: $H_2N$—$CH_2$—$(CH_2)_p$—NH—$(CH_2)_q$—$NH_2$, where p is from 1 to about 5 and q is from 1 to about 10. A second organic acid is selected from substituted and unsubstituted α, β unsaturated carboxylic fatty acids and amide and ester derivatives thereof, having from about 3 to about 11 carbon atoms, or a salt thereof; substituted and unsubstituted α, β unsaturated sulfonic and phosphonic fatty acids having from about 2 to about 11 carbon atoms, or a salt thereof; and combinations thereof.

The first organic acid and the alkyl polyamine are mixed to produce at least one intermediate compound of a general formula:

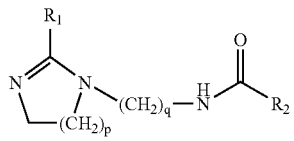

The intermediate compound and the second organic acid are then mixed to produce the compound depicted in Structure I. In preferred embodiments, p is from 1 to about 5 and q is from 1 to about 10.

It is an advantage of the invention to provide novel environmentally friendly compounds for hydrocarbonaceous deposit removal and corrosion inhibition in oil and gas applications.

An additional advantage of the invention is to provide a method of enhancing water injection rates to enhance oil and gas production.

It is another advantage of the invention to provide compounds and methods capable of keeping surface facility equipment, pipelines, downhole injection tubing and infrastructure, and pore throats around the injector clean to accept an optimum water volume thus enhancing oil and gas production.

It is a further advantage of the invention to provide a method of applying environmentally friendly deposit-removing and corrosion-inhibiting compositions to oilfield pipelines thereby preventing downtime and loss of revenue.

It is yet another advantage of the invention to provide a method of cleaning out process equipment that has a tendency to accumulate deposits.

Additional features and advantages are described herein, and will be apparent from, the following Detailed Description and Examples.

DETAILED DESCRIPTION

"Alkenyl" means a monovalent group derived from a straight, branched, or cyclic hydrocarbon containing at least one carbon-carbon double bond by the removal of a single hydrogen atom from each of two adjacent carbon atoms of an alkyl group. Representative alkenyl groups include, for example, ethenyl, propenyl, butenyl, 1-methyl-2-buten-1-yl, and the like.

"Alkoxy" means an alkyl group attached to the parent molecular moiety through an oxygen atom. Representative alkoxy groups include methoxy, ethoxy, propoxy, butoxy, and the like.

"Alkyl" means a monovalent group derived from a straight, branched, or cyclic saturated hydrocarbon. Representative alkyl groups include methyl, ethyl, n- and iso-propyl, n-, sec-, iso- and tert-butyl, and the like.

"Aryl" means substituted and unsubstituted aromatic carbocyclic radicals and substituted and unsubstituted heterocyclic radicals having about 5 to about 14 ring atoms. Representative aryls include phenyl, naphthyl, phenanthryl, anthracyl, pyridyl, furyl, pyrrolyl, quinolyl, thienyl, thiazolyl, pyrimidyl, indolyl, and the like. The aryl is optionally substituted with one or more groups selected from hydroxy, halogen, $C_1$ to $C_4$ alkyl and $C_1$ to $C_4$ alkoxy.

"Arylalkyl" means an aryl group attached to the parent molecular moiety through an alkyl group. Representative arylalkyl groups include benzyl, phenethyl, napth-1-ylmethyl, phenylpropyl, and the like.

"Hydrocarbonaceous deposit" refers to any deposit including at least one hydrocarbon constituent and forming on the inner surface of flowlines, pipelines, injection lines, wellbore surfaces, storage tanks, process equipment, vessels, the like, and other components in oil and gas applications. Such deposits also include "schmoo," which refers to a solid, paste-like, or sludge-like substance that adheres to almost any surface with which it comes in contact and is particularly difficult to remove. Deposits contributing to schmoo may include, for example, sand, clays, sulfur, naphthenic acid salts, corrosion byproducts, biomass, and other hydrocarbonaceous materials bound together with oil. These terms are used interchangeably herein.

This invention discloses heterocyclic bis-quaternized corrosion inhibiting and schmoo removing compounds having an amido moiety. For convenience, the depicted structures are shown as having tautomeric double bonds in the N—C—N linkage of the heterocyclic ring (i.e., a resonance structure). The pi electrons in the N—C—N linkage are thus delocalized between the two nitrogen atoms of the heterocyclic ring. The disclosed bis-quaternized compounds may be used alone or in combination with other corrosion inhibitors, corrosion inhibiting formulations, and/or hydrocarbonaceous deposit removing compounds and/or formulations, described in more detail below.

Preparation of Representative Compounds for the Invention is provided in Schemes 1, 2 and 3.

Scheme 1

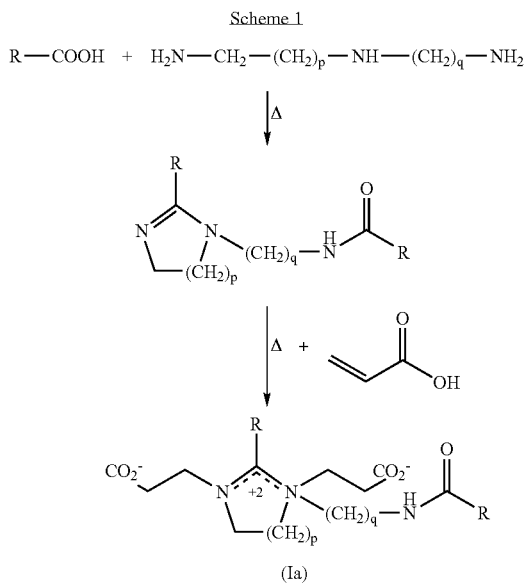

Scheme 2

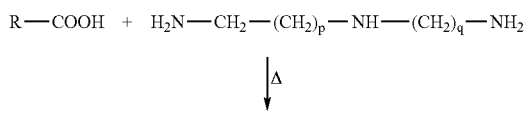

Scheme 3

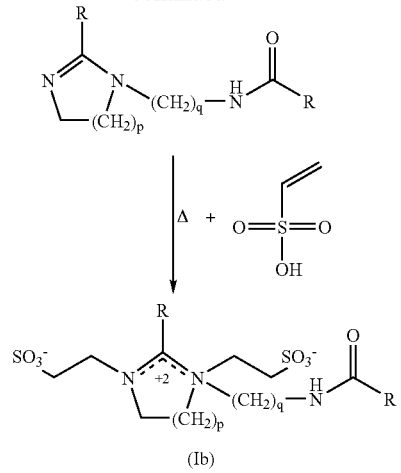

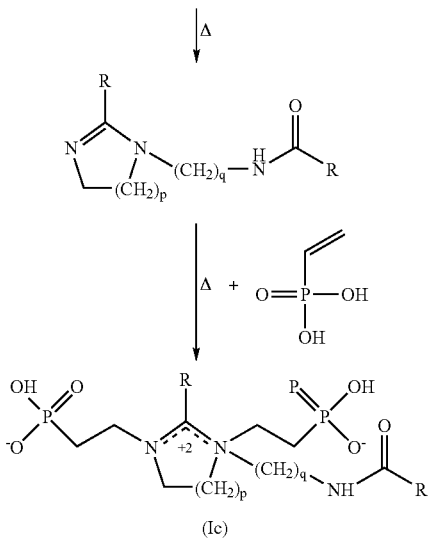

The first organic acid in the Schemes above is shown with a generalized "R—COOH." It should be appreciated that one type or a mixture of fatty acids may be used. For example, the first organic acid may include a single type of fatty acid, such as caprylic acid, nonanoic acid, capric acid, undecanoic acid, or lauric acid, which would result in Structure Ia and Ib having the same R group at both positions. Alternatively, the first organic acid may include a mixture of fatty acids, such as tall oil fatty acid or a mixture of other fatty acids, which would result in a mixture of different R substituents (as described herein for $R_1$ and $R_2$) in Structures Ia, Ib, and/or Ic.

Representative long chain fatty acids R—COOH include caprylic acid, nonanoic acid, capric acid, undecanoic acid, lauric acid, tridecanoic acid, myristic acid, palmitoleic acid, tall oil fatty acid (mixture of oleic, linoleic and linolenic acids), stearic acid, palmitic acid, arachidic acid, arachidonic acid, oleic acid, 9,11,13-octadecatrienoic acid, 5,8,11,14-eicosatetraenoic acid, eicosenoic acid, heneicosenoic acid, erucic acid, heneicosanoic acid, behenic acid, 3-methylhexadecanoic acid, 7-methylhexadecanoic acid, 13-methylhexadecanoic acid, 14-methyl-1-eicosenoic acid, derivatives thereof, the like, and mixtures thereof.

Likewise, the alkyl polyamine in the above Schemes may alternatively include one or a mixture of alkyl polyamines as described herein. For example, a preferred alkyl polyamine is diethyltriamine ("DETA"). Scheme 4 illustrates an embodiment using a mixture of tall oil fatty acid as the first organic acid, DETA as the alkyl polyamine, and acrylic acid as the second organic acid to produce Structure Ic. $R_T$—COOH represents a mixture of tall oil fatty acids, where $R_T$ is predominantly $C_{17}H_{33}$ and $C_{17}H_{31}$.

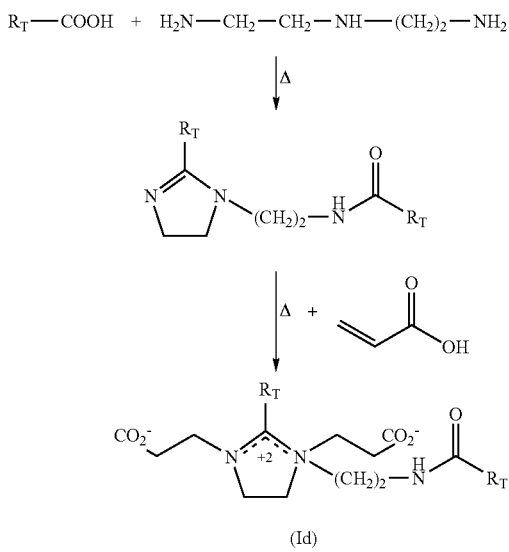

Scheme 4

Generally, alkyl polyamines that may be used to practice the invention include those having the general formula $H_2N$—$CH_2$—$(CH_2)_p$—NH—$(CH_2)_q$—$NH_2$, where p is from 1 to about 5 and q is from 1 to about 10. Preferred alkyl polyamines include those where p is from 1 to 2 and q is from 1 to 3. Most preferably, p is 1 and q is 2.

The second organic acid introduced in the representative reaction schemes generally include α, β unsaturated carboxylic fatty acids and amide and ester derivatives thereof; α, β unsaturated sulfonic and phosphonic fatty acids, and their combinations. More specifically, the second organic acid may be selected from the group consisting of substituted and unsubstituted α, β unsaturated carboxylic fatty acids and amide and ester derivatives thereof, having from 3 to about 11 carbon atoms, or a salt thereof; substituted and unsubstituted α, β unsaturated fatty acids having from 2 to about 11 carbon atoms, or a salt thereof; and combinations thereof.

Preferred α, β unsaturated fatty acids typically have from 2 to about 9 carbon atoms. In a more preferred embodiment, the α, β unsaturated fatty acids have from 2 to about 7 carbon atoms. The most preferred form of the α, β unsaturated fatty acids of the invention have from 2 to about 5 carbon atoms. It should be understood that the range of carbon atoms described refers to the main chain of the fatty acid and does not include carbon atoms that may be contributed by substituents. Examples of suitable substituents include, without limitation, hydrogen and linear or branched alkyl, aryl, alkylaryl, cycloalkyl, and aromatic or heteroaromatic groups having from 1 to about 10 carbon atoms, and their combinations.

As illustrated in the exemplary reaction schemes, to produce a composition including an amide intermediate, a molar ratio of the first organic acid to the alkyl polyamine is typically in the range of about 1.1:1 to about 500:1. In a preferred embodiment, the range is from about 1.1:1 to about 3:1. This range represents the ratio of the total number of moles of the first organic acid to the total number of moles of the alkyl polyamine used in the process for making the bis-quaternary compounds of the invention. The first step in the representative reaction schemes is similar to that disclosed in U.S. Pat. No. 6,303,079 B1, entitled, "CORROSION INHIBITOR COMPOSITIONS," which is incorporated herein by reference in its entirety.

It should be appreciated that terms used herein to depict reaction steps in reaction schemes are intended to embrace all synthesis procedures, such as batch, continuous, in situ, interfacial, solution-type, and combinations thereof. Further, such terms are used for convenience and should not be construed to limit the scope of the invention to: (i) any particular sequence of reaction steps suggested herein; or (ii) the production and/or separation of any specified amount of intermediate(s) for any specified length of time as a prerequisite to a subsequent process step.

The described intermediate mixture produced from the first organic acid and the alkyl polyamine is mixed with an organic compound of the second type to produce a bis-quaternized compound having an amido moiety. To produce a bis-quaternized compound having a moiety containing a hydrocarbon and carbonyl, sulfonyl or phosphonyl group, the amide intermediate mixture is mixed with one or more of the α, β unsaturated fatty acids or acid derivatives, described above as the second organic acid. Preferably, the relative amounts of the intermediate mixture and the second organic acid or acid derivative are determined on a mole ratio basis. The intermediate mixtures produced in the process of this invention can include other compounds in addition to the target intermediate species specified for a particular process.

Thus, a composite molecular weight can be used to calculate the number of moles of a particular intermediate mixture. Such a composite molecular weight determination could theoretically represent the molecular weights of all chemical species of the mixture and their respective mole percent contributions to the mixture composition. Making such a determination, however, requires time-consuming and tedious analysis of the mixture composition. Consequently, for convenience, the composite molecular weight for an intermediate mixture, produced by the processes of the invention, was determined herein by presuming the mixture is primarily comprised of the target species. For example, the composite molecular weight assigned to the amide compound (if p=1) mixture of the example below is 613 grams/mole (i.e., the molecular weight of the target compound). Accordingly, such composite molecular weights can be used to calculate the number of moles of the mixture, and thereby determine the preferred amount of the second organic acid to be used in view of the mole ratio ranges specified below.

For a bis-quaternized compound having an amido moiety, the mole ratio of the target amide intermediate mixture to the second organic acid or acid derivative is preferably selected from the range of from about 1:1 to about 1:5. More preferably, the mole ratio of the target amide intermediate mixture to the second organic acid or acid derivative is selected from the range of from about 1:1 to about 1:4. Most preferably, the mole ratio of the target amide intermediate mixture to the second organic acid or acid derivative is selected from the range of from about 1:1.1 or 1:2 to about 1:2.5. For complete conversion to the bis-quaternary state, a molar ratio of at least 1:2 should be used. It should be appreciated, however, that if a molar ratio of greater than 1:2.5 is used typically no more than 2.5 moles of the second organic acid reacts.

The described treating compounds/compositions (the terms "compound" and "composition" are sometimes used interchangeably herein to describe alternative embodiments) may be used in any system exposed to fluids (e.g., liquid, gas, slurry, or mixtures thereof) containing a metal corrosion agent where improved corrosion inhibition and/or schmoo removal is desired. However, the compounds of the invention are particularly well suited for use in oil and gas field applications, refinery operations, and oil and gas transmission systems. With respect to such oil and gas field applications, the described compounds are typically added to oil, water, and/or gas fluids in the form of a solution or dispersion in water or an organic solvent.

Examples of suitable solvents are alcohols such as methanol, ethanol, isopropanol, isobutanol, secondary butanol, glycols (e.g., ethylene glycol, ethylene glycol monobutyl ether, and the like), aliphatic and aromatic hydrocarbons, the like, and combinations thereof. In some embodiments, the described compounds are sparingly or fully water-soluble and as such compositions may be suitably formulated in a mixture of water and one or more alcohols or glycols. Similarly, the described compounds may be suitably formulated in an aromatic naptha, such as heavy aromatic naptha, by incorporating one or more alcohols or glycols in the composition.

The effective amount of active ingredient in a formulation required to sufficiently reduce the rate of corrosion and/or remove schmoo varies with the system in which it is used. Methods for monitoring the severity of corrosion and/or deposits in different systems are well known to those skilled in the art and may be used to decide the effective amount of active ingredient required in a particular situation. The described compounds may be used to impart the property of hydrocarbonaceous deposit removal to a composition for use in an oil or gas field application and may have one or more other functions, such as corrosion inhibition.

The described compounds are particularly effective for inhibiting corrosion of mild steel in hydrocarbon, oil/brine mixtures and aqueous systems under a variety of conditions. These compounds/compositions may be used, for example, in sweet systems (i.e., systems having a relatively high $CO_2$ concentration) or in systems having sour conditions (i.e., relatively high $H_2S$ concentration). Although the fluid content of flow lines may vary, the inhibitor may also be used in a variety of environments. Oil cuts in the field can range from less than 1% (oil field) to 100% (refinery) oil, while the nature of the water can range from 0 to 300,000 ppm TDS (total dissolved solids). In addition, the compositions of the present invention would also be useful in large diameter flow lines of from about 1 inch to about 4 feet in diameter, small gathering lines, small flow lines and headers. In a preferred method, the inhibitor composition is added at a point in the flow line upstream from the point at which corrosion prevention or schmoo removal is desired.

In practice, the compositions of the invention are typically added to the flow line to provide an effective treating dose of the described compound(s) from about 0.01 to about 5,000 ppm. In an embodiment, such doses are maintained to prevent corrosion. In another embodiment, such doses may be intermittent (i.e., batch treatment) to remove hydrocarbonaceous deposits. In a further embodiment, such doses may be continuous/maintained and/or intermittent to both inhibit corrosion and remove deposits.

In a preferred embodiment, the described composition is dosed to provide from about 0.1 to about 500 ppm of the compound(s). In a more preferred embodiment, the dose is from about 1 to about 250 ppm. Although a most preferred use of the described compounds/composition is for mild steel flow lines, it is believed that they are also effective in other types of metallurgy and at lower dosage rates.

Dosage rates for batch treatments typically range from about 10 to about 400,000 ppm. In a preferred embodiment, the flow rate of the flow line in which the composition is used is between 0 and 100 feet per second. A more preferred flow rate is between 0.1 and 50 feet per second. In some cases, the compounds of the invention may be formulated with water in order to facilitate addition to the flow line.

The described compounds may be used alone or in combination with other compounds. Typical combinations include pour point depressants and/or surfactants. Examples of suitable pour point depressants are $C_1$ to $C_3$ linear or branched alcohols, ethylene, and propylene glycol. Examples of suitable surfactants are ethoxylated nonylphenols and/or ethoxylated amines as wetting agents or additives for dispersing the compound into the fluid stream to which they are added. The surfactant is advantageously water-soluble to allow the product to better wet the surface of the flow line where corrosion may take place. Water-soluble surfactants utilized may be non-ionic, cationic, or anionic and will generally have a hydrophilic-lipophilic (HLB) value greater than 7. Oil-soluble surfactants may be utilized if it is desired to disperse the composition into a hydrocarbon fluid. Oil-soluble surfactants may be non-ionic, cationic, or anionic. These surfactants typically have an HLB value less than 7.

In alternative embodiments, formulations may include components such as phosphate esters and mercapto synergists. The composition may also include one or more suitable solvents including, but not limited to, water, monoethylene glycol, ethylene glycol, ethylene glycol monobutyl ether, methanol, isopropanol, the like, derivatives thereof, and combinations thereof.

Other compounds that may also be blended with the compositions claimed herein are quaternary amines, such as fatty, cyclic, or aromatic amines quaternized with lower alkyl halides or benzyl chloride and certain amides. In addition, filming agents, such as p-toluenesulfonic acid and dodecylbenzenesulfonic acid, may also be used. The described compositions may also contain components that are typically included in corrosion inhibiting compositions, such as scale inhibitors and/or surfactants. In some instances, it may be desirable to include a biocide in the composition.

Examples of suitable formulations are provided in Table 1.

TABLE 1

| Component | % by weight |
|---|---|
| Aromatic naptha | 0 to 75 |
| Described bis-quaternized compound(s) | 5 to 50 |
| Quaternary ammonium compound | 0 to 20 |
| Glycolic/Thioglycolic acid | 0 to 20 |
| Acetic acid | 0 to 20 |
| Water or other solvent | 0 to 95 |
| Other optional components | 0 to 95 |

Suitable quaternary ammonium compounds (quats) include a broad list, such as trialkyl, dialkyl, dialkoxy alkyl, monoalkoxy, benzyl, and imidazolinium quaternary ammonium compounds. Particularly preferred quats are noted below as this is merely a broad list of different classes of quaternary ammonium compounds that may be useful within the inventive complex and method. Representaitve quats include trialkyl quats, dialkyl quats, dialkoxy alkyl quats, monoalkoxy quats, benzyl quats, imidazolinium quats, salts thereof, the like, and combinations thereof.

The described bis-quaternary compound(s) are preferably present from about 10 to about 50 weight percent or from about 5 to about 30 weight percent. More preferably, the formulation includes from about 10 to about 30 weight percent or from about 15 to 20 to about 25 to 30 weight percent of the described bis-quaternary compound(s). The most preferred embodiment includes from about 15 to about 26 weight percent of the described bis-quaternary compound(s).

The resultant formulation(s) may be used in a variety of petroleum operations in the oil and gas industry, such as to treat systems used in primary, secondary, and tertiary oil and gas recovery. The formulation may be introduced to such systems in accordance with techniques well known to those skilled in the art. For example, one technique in which the formulation can be used is the squeeze treating technique, whereby the treating formulation is injected under pressure into a producing formation, adsorbed onto the strata, and desorbed as the fluids are produced. For example, the described formulation may be used to enhance oil and gas production by optimizing water infectivity rates in water injection systems by removing hydrocarbonaceous deposits from such systems. In some cases, optimizing water infectivity rate includes maximizing the water injection rate. Further, the formulation can be added in water flooding operations of secondary oil recovery, as well as to pipelines, transmission lines, and refinery units. The formulation may also be used to inhibit acid solution in well-acidizing operations.

It should be appreciated that the described compounds may also be applied in water injection systems as a surfactant in surfactant flooding applications, alone or in the presence of one or more surfactants, polymers, acids, or bases. For example, such a combination may be used to remove oil entrapped in formation rock capillaries. Mechanisms for removing the oil may include altering rock wettability, reducing the oil-water-rock interfacial tension, emulsifying or micro-emulsifying the oil, and others. Examples of polymers are disclosed in U.S. Pat. No. 6,729,402, entitled, "METHOD OF RECOVERING HYDROCARBON FLUIDS FROM A SUBTERRANEAN RESERVOIR."

It will be apparent to those skilled in the art that the provided examples are non-limiting and are merely illustrative. Also, the reaction schematics specifying particular intermediates and final products illustrate only those compounds presumed as significant compounds formed based on current principles of organic reaction chemistry and qualitative infrared analysis of the final reaction product. Illustration of a specified intermediate does not exclude the presence of other significant intermediate(s) important to the formation of the final product. Further, illustration of a final compound does not exclude the presence of other compounds in the final composition, including, without limitation, the unreacted starting reactants, intermediates, and other final compound(s), if any, produced by competing reaction pathways.

EXAMPLES

The foregoing may be better understood by reference to the following examples, which are intended for illustrative purposes only and are not intended to limit the scope of the invention.

Example 1

To prepare Compound Id illustrated in Scheme 4 above, 220.4 grams (0.78 moles) of a tall oil fatty acid mixture ("TOFA"—comprised of about 46% oleic acid, about 41% linoleic acid, about 4% stearic acid, and about 9% other acids) was weighed and placed into a 500 mL round bottom, four-neck flask equipped with an overhead stirrer, thermocouple, addition funnel, and Dean-Stark trap. The TOFA was heated to about 70° C. and 38.8 grams (0.38 moles) of diethylenetriamine was added dropwise, with stirring. An exotherm of about 35° C. was observed. The mixture was further heated at 130° C. for 1 hour and at 160° C. for 2 hours. The mixture was then held at 250° C. for 2 hours with a nitrogen gas sweep. 17.6 mL (~86% of the theoretical amount for 100% imidazoline formation) of water was collected. The mixture was cooled and 60.8 grams (0.84 moles) of glacial acrylic acid was added dropwise, with stirring, (exotherm 47 and 67° C). This final mixture was heated at 120 to 125° C. for 2 hours to ensure complete reaction.

Example 2

73.4 grams (0.26 moles) of TOFA was weighed into a 250 mL round bottom, four-necked flask equipped with an overhead stirrer, thermocouple, addition funnel and Dean-Stark trap. 15.6 grams (0.26 moles) of acetic acid was added, followed by dropwise addition of 26.8 grams (0.26 moles) of diethylenetriamine with stirring. An exotherm of about 70° C. was observed. The addition funnel was replaced with a nitrogen gas inlet tube and the mixture was heated at 170 to 175° C. for 1-hour, after which 8.5 mL of water was collected. The mixture was heated to 240 to 245° C. for an additional hour. A total of 13 mL (theoretical 14 mL for 92.9% conversion) of water was collected. The mixture was cooled to ambient temperature and 20.6 grams (0.286 moles) of acrylic acid was added dropwise with stirring, when an exotherm of 24 to 55° C. was observed. The mixture was heated at 120 to 125° C. for 2 hours to ensure complete reaction.

Example 3

The performance of the product produced in Example 1 as a corrosion inhibitor was evaluated with a Wheelbox Test. This test was conducted at 150° C. in a rotary oven using flat, rectangular carbon steel, water quenched, and hardened coupons. To prepare the coupons, metal surfaces were sandblasted, washed in an alcohol/toluene mixture and dried. They were then weighed and placed individually in sample bottles.

The test medium had about 20% total dissolved solids (about 10% NaCl and about 10% $CaCl_2$-300,000 ppm in chloride). The fluid was sparged with $CO_2$ and each bottle was dosed with a measured amount of the corrosion inhibitor. The coupons were then placed in the bottles, which were then charged with a $pCO_2$ of 750 psi and a $pN_2$ of 250 psi, capped, and shaken.

The oven was heated to 150° C. and the bottles were rotated in the oven for 72 hours. After cleaning and drying, the coupons were reweighed and the percent corrosion inhibition was calculated using the formula: (average blank weight loss)–100× (weight loss of treated coupon/average blank weight loss).

The amount of each tested inhibitor is indicated in Table 2 (in ppm) and was applied as an approximately 25 weight percent composition, which represents a typical commercially used formulation. Both Compositions 1 and 2 are formulations containing the subject active in addition to aromatic naptha, a quaternary ammonium compound, and thioglycolic acid. Composition 2 further includes about 8 weight percent glacial acetic acid. The control was an approximately 25 weight percent composition of a commercially available corrosion inhibitor having a quat and an amine condensate salt (available under the tradename EC1426A from Nalco® Company in Naperville, Ill.). The results in Table 2 are presented as % corrosion protection achieved at the steel surface.

TABLE 2

| Inhibitor | 10 ppm | 25 ppm | 50 ppm | 100 ppm |
| --- | --- | --- | --- | --- |
| Blank | 0 | 0 | 0 | 0 |
| Control | 7 | 45 | 68 | 68 |
| Composition 1 | 2 | 6 | 83 | 84 |
| Composition 2 | 3 | 71 | 86 | 88 |

Example 4

A flow test, known as a Dynamic Schmoo Removal Loop ("DSRL"), was set up to evaluate the efficacy of three formulations at removing hydrocarbonaceous deposits from a pipeline steel surface under flow conditions. All tests were conducted using 80 ppm of active compound in brine (recipe shown in Table 3) at 122° F.

The brine flowed through an acrylic-walled cell having internal dimensions of 20 mm side length and 40 mm height and having an inlet and outlet connection of about 3 mm internal diameter and 10 mm from the base on opposite sides of the cell. Brine flow through the cell was controlled with a peristaltic pump set at 1-liter every three minutes. A brine reservoir of about 400 mL was kept at 122° F., and the cell was placed on a stage and also held at 122° F.

A freshly polished 1018 mild steel coupon was placed in the empty cell with a known mass of schmoo (from an Alaskan pipeline source) applied to the coupon. The cell was filled with brine and circulation commenced for one hour. The coupon was then removed from the cell and air-dried and weighed. The coupons were also weighed after removing the remaining schmoo to normalize for coupon corrosion losses. Table 4 summarizes the DSRL performance data. Initial and final mass refer to mass of schmoo.

Compound 1 is as described in Example 1 (i.e., Structure Id), which was injected at a dosage of 80 ppm active, and Compound 2 is a formulation containing Compound 1 and two other components. The activity of Compound 2 was about 60% and the total dosage was based on the total product and not normalized for the lower activity level.

TABLE 3

| Salt | Amount (grams/liter) |
| --- | --- |
| KCl | 0.2250 |
| $CaCl_2 \cdot 2H_2O$ | 0.8031 |
| $SrCl_2 \cdot 6H_2O$ | 0.0578 |
| $BaCl_2 \cdot 2H_2O$ | 0.0023 |
| $MgCl_2 \cdot 6H_2O$ | 1.3284 |
| $FeCl_2 \cdot 4H_2O$ | 0.0135 |
| $NaHCO_3$ | 2.5076 |
| $Na_2SO_4$ | 0.9067 |
| $CH_3CO_2Na$ | 0.7408 |
| NaCl | 18.6793 |

TABLE 4

| Treatment | Initial Mass (grams) | Final Mass (grams) | % Schmoo Removed |
| --- | --- | --- | --- |
| Compound 1 | 0.1454 | 0.0225 | 85 |
| Compound 2 | 0.1831 | 0.0714 | 61 |

Example 5

This Example demonstrates representative environmental profiles for the described bis-quaternary compounds. The environmental impact of a production chemical is typically defined by three tests: biodegradation, bioaccumulation, and toxicity. All three criteria have limits that must be achieved in order for a chemical to be permitted for use. In order for a product to be used without restriction offshore, two of the following three criteria must be satisfied:
  (i) Test Biodegradation must be greater than 60% (if less than 20% material is automatically marked for substitution)
  (ii) Bioaccumulation as measured by Octanol/Water partitioning coefficient ($LogP_{o/w}$) must be below 3 (or molecular weight higher than 700)
  (iii) Toxicity to the most sensitive marine species (typically Skeletonema) must be greater than $LC_{50}$ or $EC_{50}$ of 10 ppm.

Three environmental screens were performed to measure toxicity, bioaccumulation and biodegradation of the described compounds inhibitors, as shown in Table 5 below. The disclosed compounds meet all the requirements to qualify as "Green."

TABLE 5

| Inhibitor | Toxicity $EC_{50}$ (ppm) | Bioaccumulation $LogP_{o/w}$ (Mol. Wt.) | Biodegradation, t = 28 days |
| --- | --- | --- | --- |
| Green | >10 | <3 (or Mw > 700) | >60% |
| Disclosed Compounds | 13.6 | Mw > 700 | 36% |

It should be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The claimed invention is:
1. A bis-quaternized compound for inhibiting corrosion and/or removing hydrocarbonaceous deposits in oil and gas applications, the compound having a net charge of zero and having a general formula:

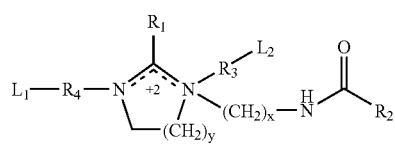

(a) wherein $R_1$, $R_2$, $R_3$, and $R_4$ are independently selected from the group consisting of: an unsubstituted branched, chain, or ring alkyl or alkenyl having from 1 to about 29 carbon atoms in its main chain; a partially or fully substituted branched, chain, or ring alkyl or alkenyl having from 1 to about 29 carbon atoms in its main chain, wherein said substitution includes being oxygenized, sulfurized, and/or phosphorylized; and combinations thereof;

(b) $L_1$ and $L_2$ is each a moiety independently selected from the group consisting of: —H, —$CO_2H$, —$SO_3H$, —$PO_3H_2$, —$CO_2R_5$, —$CONH_2$, —$CONHR_5$, —$CON(R_5)_2$, and combinations thereof; wherein each $R_5$ is independently selected from the group consisting of: branched or unbranched alkyl, aryl, alkylaryl, cycloalkyl, and heteroaromatic groups having from 1 to about 10 carbon atoms, and combinations thereof;

(c) x is from 1 to about 10; and (d) y is from 1 to about 5.

2. The bis-quaternized compound of claim 1, wherein $R_1$ and $R_2$ are derived from a mixture of tall oil fatty acids and are predominantly a mixture of $C_{17}H_{33}$ and $C_{17}H_{31}$.

3. The bis-quaternized compound of claim 2, wherein x is 2, y is 1, $R_3$ and $R_4$ are $C_2H_2$, and $L_1$ and $L_2$ are —$CO_2H$.

4. A method of improving production in an oil and/or gas application, the method comprising adding as either continuously or intermittently to a fluid in said application: (i) the compound of claim 1 in either pure or mixed solid form or (ii) a composition having from about 5 to about 50 weight percent of the compound of claim 1 dispersed or dissolved in one or more solvents; wherein the composition optionally includes one or more surfactants, polymers, acids, and/or bases.

5. The method of claim 4, wherein improving production includes reducing a corrosion rate and/or removing hydrocarbonaceous deposits from metallic surfaces in contact with the fluid.

6. The method of claim 4, wherein the composition includes from about 10 to about 50 weight percent of the compound.

7. The method of claim 4, wherein the one or more solvents includes at least one organic solvent.

8. The method of claim 4, wherein the one or more solvents are selected from the group consisting of: alcohols, glycols, aliphatic and aromatic hydrocarbons, and combinations thereof.

9. The method of claim 4, wherein the fluid includes oil or gas and water.

10. The method of claim 4, including improving water injectivity rates to optimize oil and gas production.

11. The method of claim 4, including removing hydrocarbonaceous deposits from water injection systems.

12. The method of claim 4, including removing hydrocarbonaceous deposits from components selected from the group consisting of: flowlines, pipelines, injection lines, wellbore surfaces, storage tanks, process equipment, vessels, and combinations thereof.

13. The method of claim 4, including continuously adding from about 0.01 ppm to about 5,000 ppm of the compound and/or intermittently adding from about 10 ppm to about 400,000 ppm of the compound.

14. A method of producing a corrosion inhibiting and/or hydrocarbonaceous deposit removing composition for oil and gas applications, the composition including at least one bis-quaternized compound having the general formula of claim 1, the method comprising:

(a) selecting a first organic acid from the group consisting of: unsubstituted saturated or mono- or poly unsaturated fatty acids having from 2 to about 30 carbon atoms in its main chain; partially or fully substituted saturated or mono- or poly unsaturated fatty acids having from 2 to about 30 carbon atoms in its main chain, wherein said substitution includes being oxygenized, sulfurized, and/or phosphorylized; and combinations thereof;

(b) selecting an alkyl polyamine from the group having a general formula: $H_2N-CH_2-(CH_2)_p-NH-(CH_2)_q-NH_2$, wherein p is from 1 to about 5 and q is from 1 to about 10;

(c) selecting a second organic acid from the group consisting of: substituted and unsubstituted α, β unsaturated carboxylic fatty acids and amide and ester derivatives thereof, having from 3 to about 11 carbon atoms, or a salt thereof; substituted and unsubstituted α, β unsaturated sulfonic and phosphonic fatty acids having from 2 to about 11 carbon atoms, or a salt thereof; and combinations thereof;

(d) mixing the first organic acid and the alkyl polyamine to produce at least one intermediate compound of a general formula:

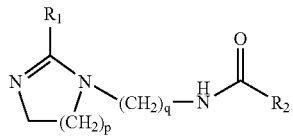

wherein $R_1$ and $R_2$ depend upon which first organic acid(s) is/are selected; and (e) mixing the intermediate compound and the second organic acid to produce the composition.

15. The method of claim 14, wherein the first organic acid includes from about 6 to about 30 carbon atoms in its main chain.

16. The method of claim 14, wherein the first organic acid is derived from a mixture of tall oil fatty acids and is predominantly a mixture of $C_{18}H_{34}O_2$ and $C_{18}H_{32}O_2$.

17. The method of claim 14, wherein the alkyl polyamine is diethylenetriamine.

18. The method of claim 14, wherein the second organic acid is acrylic acid or its salt.

19. The method of claim 14, including mixing the first organic acid and the alkyl polyamine in an approximately 1.1:1 to 3:1 mole ratio and applying heat.

20. The method of claim 14, including mixing the intermediate compound and the second organic acid in an approximately 1:2.0 to 1:2.5 molar ratio and applying heat.

* * * * *